United States Patent
Zou et al.

(10) Patent No.: US 9,687,207 B2
(45) Date of Patent: Jun. 27, 2017

(54) PRE-RECONSTRUCTION CALIBRATION, DATA CORRECTION, AND MATERIAL DECOMPOSITION METHOD AND APPARATUS FOR PHOTON-COUNTING SPECTRALLY-RESOLVING X-RAY DETECTORS AND X-RAY IMAGING

(71) Applicant: TOSHIBA MEDICAL SYSTEMS CORPORATION, Otawara-shi (JP)

(72) Inventors: Yu Zou, Naperville, IL (US); Xiaolan Wang, Buffalo Grove, IL (US); Adam Petschke, Lake Bluff, IL (US); Chunguang Cao, Buffalo Grove, IL (US); Yuexing Zhang, Naperville, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 88 days.

(21) Appl. No.: 14/676,594

(22) Filed: Apr. 1, 2015

(65) Prior Publication Data
US 2016/0287205 A1    Oct. 6, 2016

(51) Int. Cl.
*A61B 6/03*    (2006.01)
*A61B 6/00*    (2006.01)
*G06T 11/00*    (2006.01)

(52) U.S. Cl.
CPC ............. *A61B 6/585* (2013.01); *A61B 6/032* (2013.01); *A61B 6/4241* (2013.01);
(Continued)

(58) Field of Classification Search
CPC ........... A61B 6/03; A61B 6/032; A61B 6/482; A61B 6/5205; A61B 6/5211;
(Continued)

(56) References Cited

U.S. PATENT DOCUMENTS 7,208,739 B1 * 4/2007 Yanoff .................... G01T 1/171
  250/363.09
7,734,076 B2 * 6/2010 Du .......................... A61B 6/032
  378/16

(Continued)

OTHER PUBLICATIONS

Yu Zou, et al., "Analysis of Fast kV-switching in Dual Energy CT using a Pre-reconstruction Decomposition Technique" Medical Imaging 2008: Physics of Medical Imaging, vol. 6913, 2008, pp. 69131-1-691313-12.

*Primary Examiner* — David E Smith
(74) *Attorney, Agent, or Firm* — Oblon, McClelland, Maier & Neustadt, L.L.P.

(57) ABSTRACT

An apparatus and method of processing X-ray projection data obtained using photon-counting detectors and having multiple spectral components. The processing of the projection data includes correcting for nonlinear detector response, where the detector response model includes: pileup, ballistic deficit effects, polar effects, and characteristic X-ray escape. The processing of the projection data also includes a material decomposition mapping the projection data from spectral components into material components corresponding to high-Z and low-Z materials. The material decomposition includes a noise balancing process where the allocation of spectral components between a high-energy and a low-energy combination of spectral components is adjusted such that both high- and low-energy components have signal-to-noise ratios of similar magnitude. For computed tomography (CT) applications, material decomposition can be followed by image reconstruction and then image post-processing and presentation. For non-CT applications, material decomposition can be followed by image post-processing and presentation.

17 Claims, 9 Drawing Sheets

(52) U.S. Cl.
CPC .......... *A61B 6/4266* (2013.01); *G06T 11/005* (2013.01); *A61B 6/405* (2013.01); *A61B 6/482* (2013.01); *A61B 6/5205* (2013.01)

(58) Field of Classification Search
CPC ....... A61B 6/5285; A61B 6/585; G06T 5/002; G06T 11/005; G06T 2207/10016; G06T 2207/10116; G06T 2211/421; G06T 2211/424
See application file for complete search history.

(56) References Cited

U.S. PATENT DOCUMENTS

| | | |
|---|---|---|
| 8,965,095 B2 | 2/2015 | Zou et al. |
| 9,256,938 B2 | 2/2016 | Petschke et al. |
| 2007/0237288 A1* | 10/2007 | Tkaczyk ................ A61B 6/032 378/5 |
| 2008/0137803 A1* | 6/2008 | Wu ........................ A61B 6/032 378/5 |
| 2008/0298544 A1* | 12/2008 | Dugan ................. G06K 9/6263 378/53 |
| 2009/0262997 A1* | 10/2009 | Zou ....................... G06T 11/005 382/131 |
| 2010/0189212 A1 | 7/2010 | Zou |
| 2013/0251097 A1 | 9/2013 | Zou |
| 2013/0287279 A1* | 10/2013 | Roessl ................. G06T 11/006 382/131 |
| 2013/0291097 A1 | 10/2013 | Tsukamoto et al. |
| 2014/0314211 A1 | 10/2014 | Zou et al. |
| 2015/0117596 A1* | 4/2015 | Cao ....................... A61B 6/5264 378/20 |
| 2015/0160355 A1 | 6/2015 | Wang et al. |
| 2016/0070008 A1 | 3/2016 | Cao et al. |
| 2016/0131773 A1 | 5/2016 | Cao et al. |

* cited by examiner

PRE-RECONSTRUCTION CALIBRATION, DATA CORRECTION, AND MATERIAL DECOMPOSITION METHOD AND APPARATUS FOR PHOTON-COUNTING SPECTRALLY-RESOLVING X-RAY DETECTORS AND X-RAY IMAGING

BACKGROUND

Field

This disclosure relates to data processing of X-ray projection data obtained using spectrally-resolving photon-counting X-ray detectors for both computed tomography (CT) and non-CT applications, and more particularly relates to the data processing steps of calibration, correcting for detector artifacts, measurement artifacts, and performing material decomposition of X-ray projection data.

Description of the Related Art

Computed tomography (CT) systems and methods are widely used, particularly for medical imaging and diagnosis. CT systems generally create images of one or more sectional slices through a subject's body. A radiation source, such as an X-ray source, irradiates the body from one side. A collimator, generally adjacent to the X-ray source, limits the angular extent of the X-ray beam, so that radiation impinging on the body is substantially confined to a planar region defining a cross-sectional slice of the body. At least one detector (and generally many more than one detector) on the opposite side of the body receives radiation transmitted through the body substantially in the plane of the slice. The attenuation of the radiation that has passed through the body is measured by processing electrical signals received from the detector.

Conventionally, energy-integrating detectors have been used to measure CT projection data. Now, recent technological developments are making photon-counting detectors a feasible alternative to conventional energy-integrating detectors. Photon-counting detectors have many advantages including their capacity for preforming spectral CT. To obtain the spectral nature of the transmitted X-ray data, the photon-counting detectors split the X-ray beam into its component energies or spectrum bins and count a number of photons in each of the bins. Since spectral CT involves the detection of transmitted X-rays at two or more energy levels, spectral CT generally includes dual-energy CT by definition.

Many clinical applications can benefit from spectral CT technology, which can provide improvement in material differentiation and beam hardening correction. Further, semiconductor-based photon-counting detectors are a promising candidate for spectral CT, which is capable of providing better spectral information compared with conventional spectral CT technology (e.g., dual-source, kVp-switching, etc.).

Photon-counting detectors are configured to acquire the spectral nature of the X-ray source. To obtain the spectral nature of the transmitted X-ray data, the photon-counting detector counts a number of photons in each of a plurality of energy bins. The use of the spectral nature of the X-ray source in CT is often referred to as spectral CT. Since spectral CT involves the detection of transmitted X-rays at two or more energy levels, spectral CT generally includes dual-energy CT by definition.

Semiconductor based photon-counting detectors used in spectral CT can detect incident photons and measure photon energy for every event. However, due to factors such as interaction depth and ballistic deficit, the measured photon energy cannot be related to incident photon energy uniquely. Furthermore, at high flux, pulse-pileup may also cause a loss in photon count and a distortion in photon energy. Accordingly, accurate image reconstruction can be achieved by efficiently estimating parameters of a response function of the photon-counting detectors.

There are several effects that can cause the detected spectrum to deviate from the X-ray spectrum incident on the photon-counting detectors, including: pileup (i.e., multiple detection events occurring within the detector response time), ballistic deficit effects, polar effects, characteristic X-ray escape, and space-charge effects.

Regarding pileup and ballistic deficit, due to the dead time (~100 ns), which is determined by the type of semiconductor (e.g. CZT or Cd Te), the semiconductor thickness and readout circuitry, pulse pileup at high X-ray flux (~$10^8$ cps/mm$^2$) can be very severe, and the measured spectral signals can be distorted. The distorted spectral signal can cause artifacts in the reconstructed images. Furthermore, the dead time is not a constant for a given readout circuit due to the location of the pulse formation within the detector cell. However, if the pileup effect can be corrected in the detector model, then image quality can be improved.

Regarding the polar effect, when X-ray radiation is incident on a detector element at an oblique angle rather than normal incidence, then X-rays will enter the detector element through multiple faces of the detector element. The pileup and ballistic deficit will depend on which face the X-rays enter through. Thus, a detector response model benefits from including the differences in the pileup and ballistic deficit due to oblique X-rays illuminating multiple faces of the detector (i.e., the polar effect).

Regarding characteristic X-ray escape, when high energy photons impinge on a detector, the inner shell electrons from atoms of the detector are ejected from the atom as "photoelectrons." After the ionization or excitation, the atom is in an excited state with a vacancy (hole) in the inner electron shell. Outer shell electrons then fall into the created holes, thereby emitting photons with energy equal to the energy difference between the two states. Since each element has a unique set of energy levels, each element emits a pattern of X-rays characteristic of the element, termed "characteristic X-rays." The intensity of the X-rays increases with the concentration of the corresponding element.

In many materials such as Cadmium Telluride (CdTe) or Cadmium Zinc Telluride (CZT) or the like, the characteristic X-rays primarily involve K-shell (closest shell to the nucleus of an atom) electrons. If the characteristic X-rays escape from the detector, the detector signal is incorrect and the loss of energy incurred manifests itself as errors in the output spectrum of the detectors. Thus, the measured spectral signal can be distorted and may cause artifacts in the reconstructed image.

Uncorrected, each of the discussed measurement/detector artifacts distorts the detected spectrum relative to the incident spectrum ultimately degrading the quality of reconstructed images and the material decomposition derived from the data.

One advantage of spectral CT, and spectral X-ray imaging in general, is that materials having atoms with different atomic number Z also have different spectral profiles for attenuation. Thus, by measuring the attenuation at multiple X-ray energies, materials can be distinguished and the attenuation can be attributed to a particular atom (i.e., effective Z). This attribution enables spectral projection data to be mapped from the spectral domain to the material domain using a material decomposition. In some instances, this material decomposition is performed using a dual-energy analysis method.

The dual-energy analysis method can be used because the attenuation of X-rays in biological materials is dominated by two physical processes (i.e., photoelectric absorption and Compton scattering). Thus, the attenuation coefficient as a function of energy can be approximated by the decomposition $$\mu(E,x,y) = \mu_{PE}(E,x,y) + \mu_C(E,x,y),$$

where $\mu_{PE}(E, x, y)$ is the photoelectric attenuation and $\mu_C(E, x, y)$ is the Compton attenuation. This attenuation coefficient can be rearranged instead into a decomposition of a high-Z material (i.e., material 1) and a low-Z material (i.e., material 2) to become $$\mu(E,x,y) \approx \mu_1(E)c_1(x,y) + \mu_2(E)c_2(x,y),$$

wherein $c_{1,2}(x,y)$ are spatial functions describing how much the imaged object located at position (x,y) is represented by materials 1 and 2, respectively.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1:
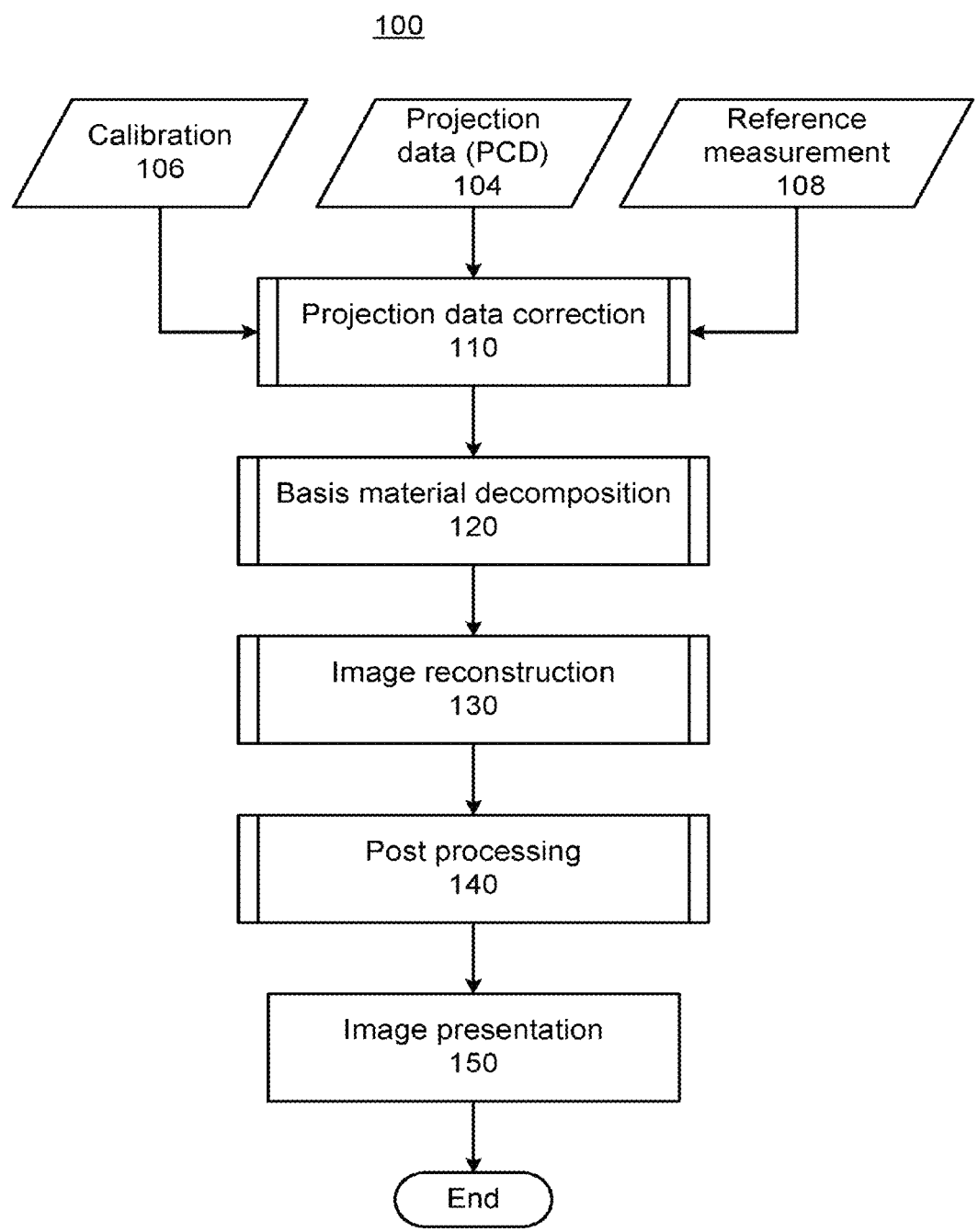
FIG. 1 shows a flow diagram of an implementation of a computed tomography data processing method.

Referring now to the drawings, wherein like reference numerals designate identical or corresponding parts throughout the several views, FIG. 1 shows a flow diagram of a method for reconstructing an image of an object OBJ based on a series of projection measurements of the object OBJ performed at different projection directions (i.e., computed tomography (CT) using projective measurements). The data processing is a product of three inputs, including: calibration values 106, projection data 104, and reference measurement values 108. The projection data have multiple spectral components, making it compatible with material decomposition based on the different spectral absorption characteristics of high-Z and low-Z materials (i.e., greater contribution of photoelectric absorption for bone (high-Z) than for water (low-Z)). In addition to being applicable to CT applications as shown in FIG. 1, processes 110 and 120 are also applicable to non-CT applications involving projective measurements, including radiography, mammography, and tomosynthesis.

The first process 110 of the image reconstruction method 100 corrects the projection data for nonlinearities, loss mechanisms, and other aspects of the detectors and the measurement process. This can include applying various calibration values 106 and reference measurement values 108 to the projection data.

Next, the method 100 proceeds to process 120 wherein the spectral projection data is decomposed from spectral components into material components while still in the projection domain. While it is possible to first reconstruct images of the object OBJ using spectral components and then perform material decomposition in the image domain (swapping the order of process 120 with process 130 contrary to the order illustrated in FIG. 1), this alternative order of the processing steps will not be considered herein. Although processes 110 and 120 are conceptually distinct, in practice (as is discussed later) the execution of processes 110 and 120 can overlap or blend together in certain implementations of method 100.

After process 120, the method 100 proceeds to process 130 wherein multiple images are reconstructed using an image reconstruction process (e.g., an inverse Radon transformation). The image reconstruction can be performed using a back-projection method, a filtered back-projection, a Fourier-transform-based image reconstruction method, an iterative image reconstruction method (e.g., algebraic reconstruction technique or the like), a matrix-inversion image reconstruction method, or a statistical image reconstruction method. For non-CT applications (e.g., radiography, mammography, and tomosynthesis) the process 130 is omitted, and the non-CT application can proceed directly from process 120 to process 140.

After process 130, the method 100 proceeds to process 140 wherein post-processing steps are performed on the data, including: volume rendering, smoothing, filtering, and various methods for combining the material images to convey physical concept (e.g., maps of the attenuation, density, or effective Z density).

Finally, in step 150 of method 100 the image is presented to a user. The image presentation can be performed by displaying the image on a digital screen (e.g., LCD monitor), by printing the image on a suitable medium (e.g., paper or an X-ray film), or by storing the image on a computer-readable medium.

The discussion herein is focused primarily on process 110 and process 120. These processes are applicable to both CT and non-CT applications.

The projection data correction process 110 is based on a detector response function, which is a modeled by the detected energy $S_{out}(E)$ derived from the energy spectrum incident on the detector $S_{in}(E)$, wherein an implementation of the detector response function is given by $$S_{out}(E) = ne^{-n\tau} \int dE_0 R_0(E,E_0) S_{in}(E_0) + n^2 e^{-n\tau} \iint dE_0 dE_1 R_1(E,E_0,E_1) S_{in}(E_0) S_{in}(E_1)$$

wherein $R_0$ is the linear response function, $R_1$ is the quadratic response function representing first-order pileup, and $\tau$ is the dead time of the detector. Each of $R_0$, $R_1$, and $\tau$ can depend on the detector element and the incident angle of the X-ray radiation. The incident spectrum is given by $$S_{in}(E_i) = S_{air}(E)\exp[-\mu_1(E)L_1 - \mu_2(E)L_2],$$

wherein $\mu_1$ and $\mu_2$ are the attenuation coefficients of the basis materials for the material decomposition, $L_1$ and $L_2$ are the projection lengths. The X-ray flux n for each detector is given by $$n = n_{air} \int dE_0 S_{in}(E_0) \exp[-\mu_1(E_0)L_1 - \mu_2(E_0)L_2],$$

wherein $n_{air} = A \cdot I_{ref}$ is the calculated flux based on a reference intensity measurement $I_{ref}$ of an X-ray source and A is a calibration value. The factor $n_{air}$ represents the X-ray flux at the detector for projective measurements taken in the absence of an imaged object OBJ (i.e., in the presence of air as an image object OBJ). A unique value of $I_{ref}$ is measured by a detector near the X-ray source for each projection angle.

The number of counts in a given energy bin is calculated by the expression $$N_m = T \int dE w_m(E) S_{Det}(E),$$

wherein T is the integration time and $w_m(E)$ is the spectral function of the $m^{th}$ energy bin of the photon counting detectors. For example, the spectral function could be a square function, which is defined as $$w_m(E) = \begin{cases} 1 & E_{m1} < E < E_{m2} \\ 0 & \text{otherwise} \end{cases}.$$

The values expressed by the symbols $R_0$, $R_1$, and $\tau$, $\mu_1$, $\mu_2$, A, $I_{ref}$, $S_{air}$, $L_1$ and $L_2$ can be categorized into four types: (1) constant values (fixed prior to calibrations or projective measurements), (2) calibration values (determined by calibrations performed prior to projection measurements on imaged object OBJ), (3) reference values (calibrations during the projection measurements on imaged object OBJ), and (4) result values (values being solved for when the detector model is solved).

The constants are the attenuation coefficients $\mu_1$, and $\mu_2$, which are determined by established models for the chosen high-Z (e.g., bone) and the low-Z (e.g., water) materials. There is only one reference value—the reference intensity $I_{ref}$. The results values are the projection lengths $L_1$ and $L_2$. Thus, all other values/functions (i.e., $R_0$, $R_1$, $\tau$, A, and $S_{air}$) are calibration values.

Figure 2:
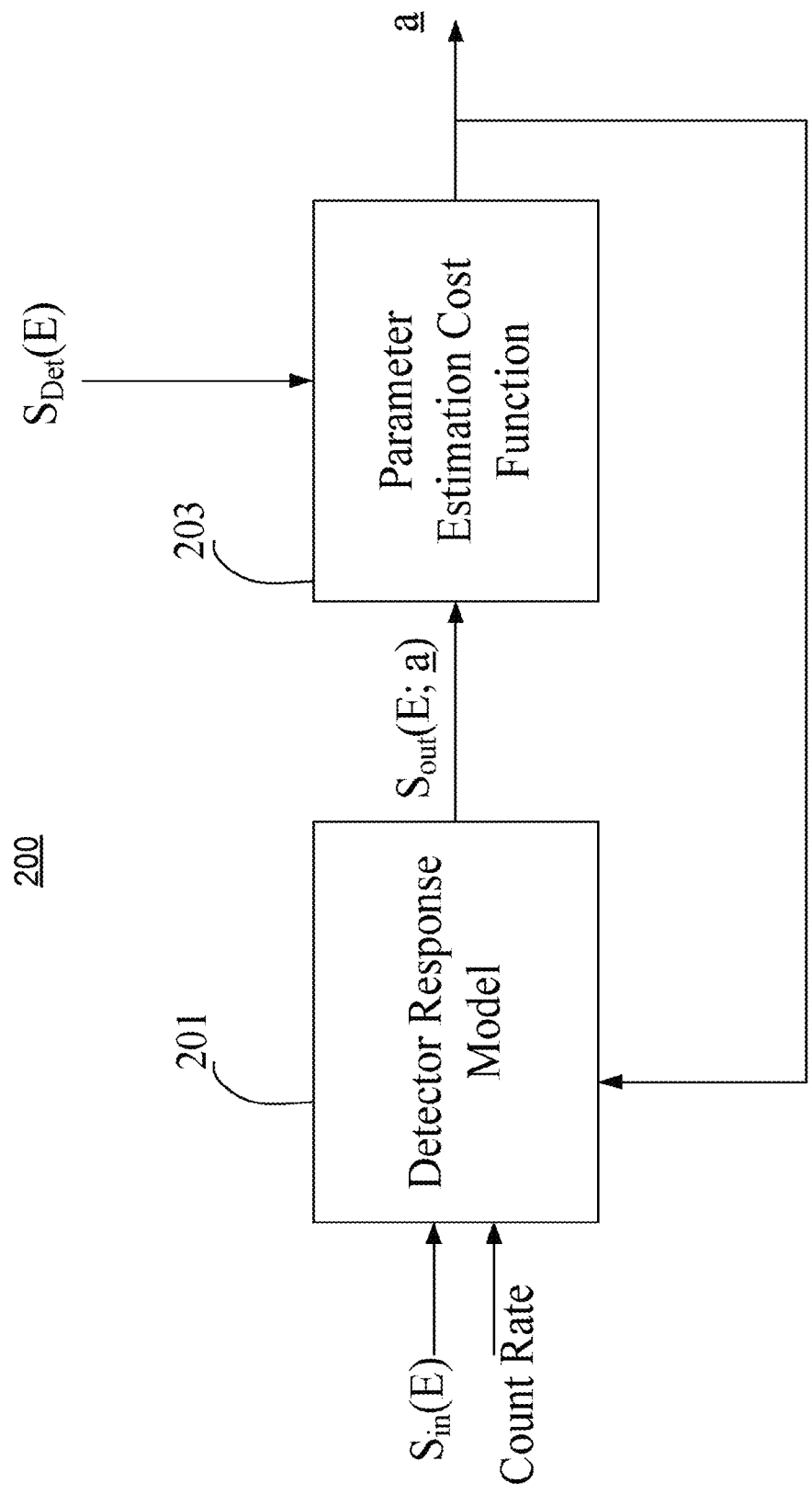
FIG. 2 shows a flow diagram of an implementation of a calibration parameter estimation method.

FIG. 2 shows as implementation of a method 200 of determining $R_0$, $R_1$, and $\tau$, according to U.S. patent application Ser. No. 14/479,955 incorporated herein by reference in its entirety. In U.S. patent application Ser. No. 13/866,965, incorporated herein by reference in its entirety, the method 200 is applied to determining calibration constants. In U.S. patent application Ser. No. 14/535,396, incorporated herein by reference in its entirety, the ballistic deficit model is expanded to include polar effects. By including polar effects, the detector model is generalized to include variations in the detector response when the X-ray radiation impinges the detectors at angles deviating from normal incidents.

Models accounting for pileup and the ballistic effect describe how the recorded spectrum $S_{out}$ differs from the incident spectrum $S_{in}$ due to multiple detection events occurring within a given detection window (i.e., the response time of the detector), resulting in a larger detection signal resulting from the combination of photoelectrons coming from multiple detection events being attributed to a single detection event. Therefore, pileup shifts the recorded spectrum $S_M$ towards higher energies because higher energies arising from multiple detections (i.e. the pileup of detection events within a detection time window) are tallied as high-energy single detection events. Thus, the detected spectrum $S_{out}$ deviates from the incident spectrum $S_{in}$.

In contrast, characteristic X-ray escape causes the recorded spectrum $S_{out}$ to shift towards lower energies relative to the incident spectrum $S_{in}$ because some of the energy absorbed into the semiconductor in a detection event is reemitted as a characteristic X-ray. Thus, rather than all of the absorbed X-ray energy being applied to creating photoelectrons, some of the energy is reemitted at a characteristic energy corresponding to the difference between an empty inner electron shell (e.g., the K-, L-, or M-shell) and an outer shell. The characteristic X-ray escape is often referred to as K-escape due to the characteristic X-ray energy typically corresponding to the K-edge. The detector model for K-escape is described in U.S. patent application Ser. No. 14/190,170, incorporated herein by reference in its entirety.

Figure 3:
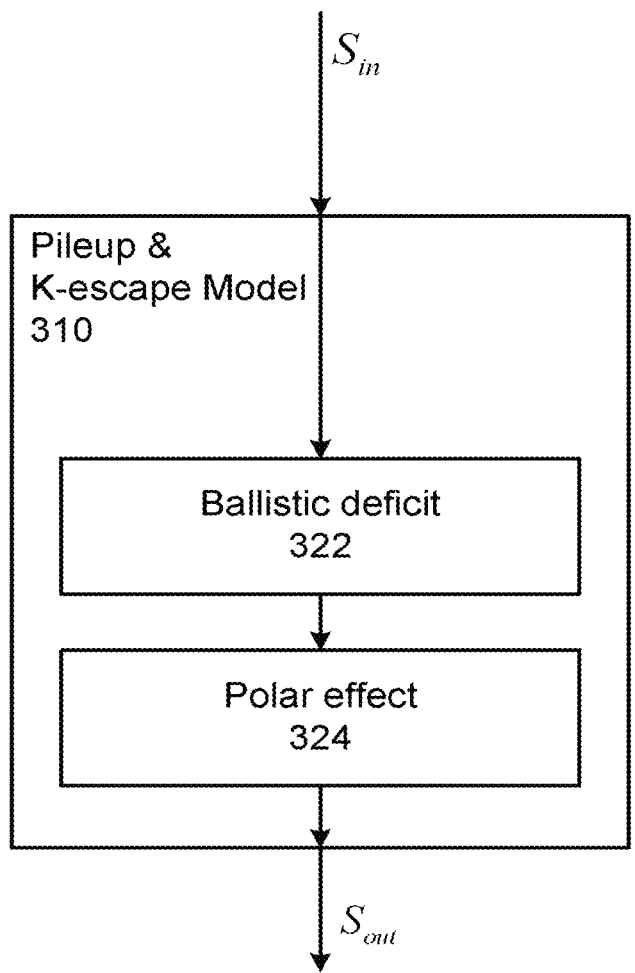
FIG. 3 shows a flow diagram of an implementation of a method for calculating a detector response model.

FIG. 3 shows an implementation of a process 310 that models the combined effects of the energy spectrum distortions arising from characteristic pileup, ballistic deficit, and polar effects. The first step 322 of process 310 accounts for the ballistic deficit, and step 324 of process 310 accounts for the spectral shifts arising from the polar effect.

In one implementation, without considering K-escape, the probability that energy E is deposited at depth $z_0$ is, $$S_{dep}(E, z_0) = S_{in}(E) e^{-\mu_{CZT}(E) z_0 / \sin\beta} \frac{\mu_{CZT}(E)}{\sin\beta}.$$

Returning to FIG. 2, the diagram illustrates an apparatus for determining a detector pileup model for each photon-counting detector in a spectral CT scanner. In particular, FIG. 2 illustrates a detector pileup model 201 that receives an incident spectrum $S_{in}(E)$, a count rate, and a parameter vector $\underline{a}$. Based on the received values, the detector pileup model 201 generates a simulated measured spectrum $S_{out}(E; \underline{a})$, wherein $\underline{a}$ includes $R_0$, $R_1$, and $\tau$. The process of determining the simulated measured spectrum $S_{out}(E; \underline{a})$ will be described in more detail below.

As shown in FIG. 2, the model parameter estimation cost function 203 compares the simulated measured spectrum $S_{out}(E; \underline{a})$ with an actual measured spectrum $S_{Det}(E)$, and updates a parameter vector $\underline{a}$ so as to minimize a predetermined cost function. The updated parameter vector $\underline{a}$, which includes $R_0$, $R_1$, and $\tau$, is fed back to the detector pileup model to generate a new simulated measured spectrum $S_{out}(E; \underline{a})$. This process continues for a predetermined number of iterations or until the change in the parameter vector $\underline{a}$ falls below a predetermined threshold. A respective optimal parameter $\underline{a}$ is found for each photon-counting detector in a scanner.

The input spectrum $S_{in}(E)$ can be determined by calculation (all vendors have models to calculate the output from their tubes) or measurements (by using a gold-standard spectroscopic detector, e.g., a high-purity germanium spectrometer) for each PCD in a scanner. The measured spectrum $S_{Det}$ is the output spectrum from each PCD corresponding to each incident spectrum. Where different X-ray sources are used for calibration measurements and for projection measurements of the imaged object OBJ, then $S_{in}(E)$ and $S_{air}(E)$ will be different. However, where the same X-ray source is used for both calibration and projection measurements, then $S_{in}(E)$ is $S_{air}(E)$. Whether or not the X-ray source for projection measurements is also used for calibrations, $S_{air}(E)$ is determined prior to the projection measurements of the imaged object OBJ. $S_{air}(E)$ may be determined in a similar manner to $S_{in}(E)$ is determined. One of ordinary skill in the art will recognize many ways of obtaining $S_{air}(E)$.

The parameter vector $\underline{a}$ includes a dead time value $\tau$, a time threshold T to determine whether, e.g., double photon events are peak pileup events or tail pileup events (although this threshold applies to determining whether a peak- or tail-pileup event occurs at any pileup order), and individual probabilities of different number of quasi-coincident photons $\chi_0$, $\chi_1^P$, $\chi_1^t$, $\chi_2^P$, $\chi_2^t$, etc. For example, $\chi_0$ is the probability of single photon events, $\chi_1^P$ is the probability of peak double pileup events, $\chi_1^t$ is the probability of tail double pileup events, $\chi_2^P$ is the probability of triple peak pileup events, etc. Note that, in practice, the contribution of higher order spectra drops quickly with increasing order and, in most embodiments, those spectra can be ignored in calculating the summed spectrum. Note that the sum of individual probabilities will be equal to or less than 1.

For the no pileup case, the first component spectrum is calculated as follows. The component spectrum becomes:

$$S_0(E) = e^{-n\tau_d} \iint dz_0 dE_0 \chi_0 S_{dep}(E_0,z_0) \delta(E - v_p(t_{TOF}^0; z_0, E_0))$$

wherein the integration runs over the whole volume with the energy condition determined by $\delta(\cdot)$ the Dirac delta function. The time of flight $t_{TOF}^0$ and the pre-amplifier voltage $v_p$ are described in U.S. patent application Ser. No. 13/866,965.

For peak pileup, the spectrum is $$S_1^P(E) = n e^{-n\tau_d}$$
$$\int\int\int\int\int dz_0 dE_0 dt_1 dz_1 dE_1 \chi_1^P S_{dep}(E_0,z_0) S_{dep}(E_1,z_1) \times$$
$$\delta\left(E - v_p(t_{TOF}^0; z_0) e^{-\frac{t_{max}-t_{TOF}^0}{\tau_p}} - v_p(t_{TOF}^1; z_1) e^{-\frac{t_{max}-t_{TOF}^1-t_1}{\tau_p}}\right).$$

Similar spectra can be calculated for tail pileup and higher order pileup. The total output spectrum then becomes the sum of each of the individual pileup components, $$S_{out} = S_0(E) + S_1^P(E) + S_1^{t0}(E) + S_1^{t1}(E) + S_2^P(E) + \ldots$$

Figure 4:
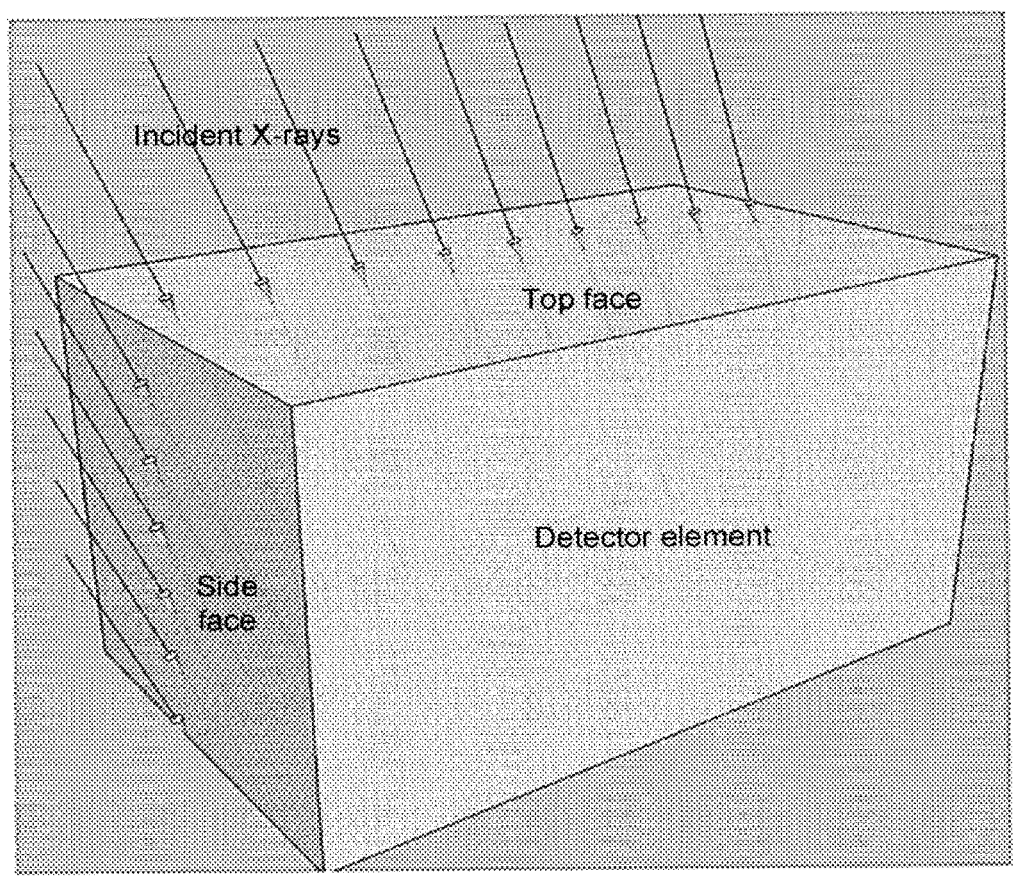
FIG. 4 shows an implementation of X-ray radiation entering a detector element at an oblique angle.

The ballistic deficit detector model from U.S. patent application Ser. No. 13/866,965 can be improved by incorporating a polar effect model from U.S. patent application Ser. No. 14/535,396. The polar effect model generalizes the ballistic deficit model to include the case where oblique X-rays enter a detector element through faces other than the front face of the detector, as shown in FIG. 4. The polar effect is included by modifying the ballistic deficit expressions for expressions for $S_0(E)$, $S_1^P(E)$, $S_1^{t0}(E)$, etc. to include the effect that some X-rays deviating from normal are incident on different faces of the detector. Further, X-rays incident on different detector faces have different propagation lengths through the detector material and different migration lengths for photoelectrons from their point of origin to the anode of the detector. These differences result in different linear and nonlinear detector response functions.

For example, FIG. 4 shows an example of a detector element with incident X-rays deviating from normal incidence. The X-rays are incident on both the top surface and the side surface. Those X-rays incident and absorbed on the side surface have, on average, shorter propagation lengths in the semiconductor of the detector element and a short distance between the origin of the photoelectrons and the detector anode.

Therefore the linear and nonlinear detector response and the corresponding models can change depending on the X-ray angle incidence. Details of how the detector response model can be modified to include the polar effect are described in U.S. patent application Ser. No. 14/535,396, which describes how these polar angle corrections can be applied to the expressions discussed for detector response based on the ballistic deficit.

In one implementation, the calibrations also include a method for reference calibration, as discussed in U.S. patent application Ser. No. 14/103,137, incorporated herein by reference in its entirety. A reference calibration is utilized to establish a mapping between a reference detector signal and a true count incident on a photon-counting detector. The true count rate/flux is then utilized to determine projection data from the detector, which is in turn utilized to generate images.

Figure 5:
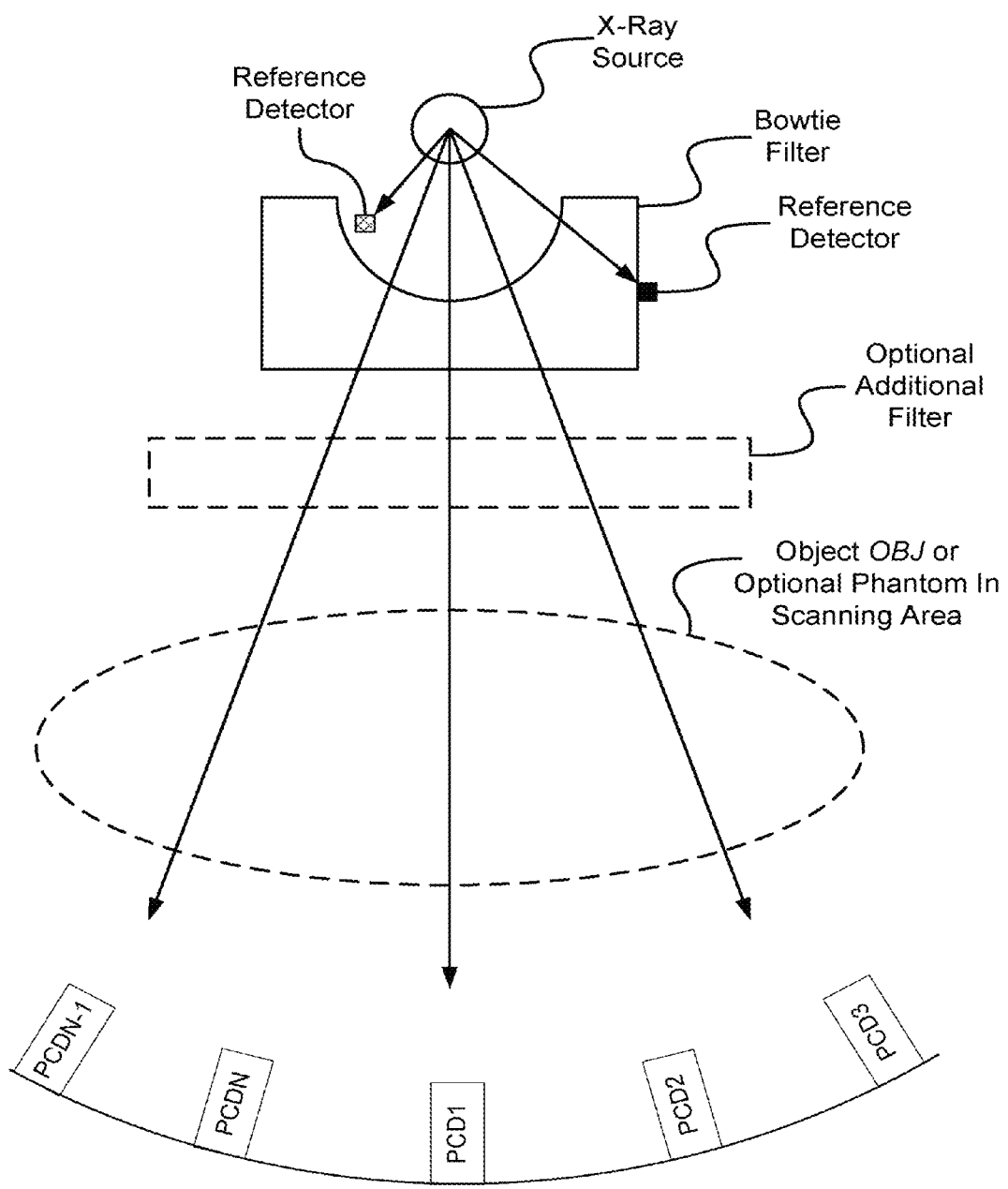
FIG. 5 shows a schematic of an implementation of a reference detector in an X-ray imaging apparatus.

FIG. 5 illustrates a CT scanner that utilizes a reference detector to monitor a variation of the X-ray source during a scan. The CT scanner generally includes an X-ray source, a bowtie filter, a reference detector, and an arrangement of photon counting detectors (PCDs) shown as PCD1 through PCDN, where PCDN is the $N^{th}$ PCD. The imaged object OBJ is positioned between the X-ray source and the PCDs. As illustrated in FIG. 5, the reference detector can be located between the bowtie filter and the object in one implementation. The reference detector can also be located between the X-ray source and the bowtie filter, as also illustrated in FIG. 5. In these and other implementations, the reference detector can be installed so as to rotate with the bowtie filter and the X-ray source. Further, multiple reference detectors can be provided, and outputs thereof can be used to create an average reference signal that is used for reference calibration. Also, multiple reference calibrations can be obtained by using multiple reference detectors, where the reference calibrations can be averaged or statistically changed to obtain a summary reference calibration.

According to aspects of implementations of this disclosure, an additional filter can be additionally/optionally included. Further, a phantom can be additionally/optionally included, as illustrated in FIG. 5. Also, in one implementation, the bowtie filter can be removed or not used.

In one implementation, the CT scanner can use a non-spectral reference detector. The reference detector is an energy-integrating detector, and only measures X-ray intensity variations. The reference detector does not measure spectrum variation.

For a given incident spectrum, the following relationship exists: $n_{PCD}^{air} \propto I_{ref}$.

A signal from an energy-integrating reference detector is $I_{ref} = T \cdot n_{ref}^{air} \cdot \int dE \cdot E \cdot S_{ref}(E)$, where T is the integration time, $n_{ref}^{air}$ is the count rate at the reference detector, E is the energy factor, and $S_{ref}(E)$ is the normalized spectrum at the reference detector. From FIG. 5, given a same spectrum, $n_{PCD}^{air} \propto n_{ref}^{air}$ since they only differ by geometrical factors (i.e., different distances to the X-ray tube) and attenuation paths to the X-ray tube (different bowtie paths, filter paths, etc.). Therefore, $n_{PCD}^{air} \propto I_{ref}$.

A constant A is determined such that $n_{PCD}^{air} = A \cdot I_{ref}$, where $I_{ref}$ is the reference detector signal (arbitrary unit), and $n_{PCD}^{air}$ is the true count rate (i.e., the true count rate across all energies) on the PCD without an object. $n_{PCD}$ is then determined from $n_{PCD}^{air}$ and a basis material thickness $\{L_1, L_2\}$ according to $$n_{PCD} = n_{PCD}^{air} \cdot \int dE \cdot S^{air}(E) e^{-\mu_1(E)L_1 - \mu_2(E)L_2},$$

where $S^{air}(E)$ is the normalized X-ray source spectrum in the absence of the object OBJ (i.e., the object OBJ is replaced by air), which spectrum $S_{air}(E)$ is known to the manufacturer.

Having determined each of the calibration values $R_0$, $R_1$, $\tau$, $A$, and $S_{air}$ during the calibration measurements and analysis, the next step of method 100 is to perform the projection data correction process 110. In process 110 the correction factor is given by $$N_m^{Corr.} = N_m^{Raw} - N_m^{Nonlin.}$$

where $N_m^{Corr.}$ is the corrected count value of the $m^{th}$ energy bin of the PCD, $N_m^{Raw}$ is the raw count value recorded from the detector, and $N_m^{Nonlin.}$ is the calculated count from the nonlinear detector response. In order to calculate $N_m^{Nonlin.}$ the values for the projections lengths $L_1$ and $L_2$ have to be assumed.

The nonlinear count value $N_m^{Nonlin.}$ is calculated according to $$N_m^{Nonlin.} = \int dE w_m(E) S_{Nonlin.}(E),$$

where, in one implementation, the nonlinear spectrum correction is given by the first order pileup $$S_{Nonlin.}(E) = S_{1,out}(E) n^2 e^{-n\tau} \iint (dE_0 dE_1 R_1(E, E_0, E_1) S_{in}(E_0) S_{in}(E_1).$$

In another implementation, the nonlinear spectrum correction includes higher-order pileup terms.

In one implementation, the nonlinear correction can be expressed as $$S_{Corr.}(E) = S_{Raw}(E) - S_{1,out}(E).$$

In one implementation, the energy spectrum distortion due to the linear term in the detector response model can also be corrected. For example, in the case that the detector counts are arranged into five energy bins, the linear response of the detector can be expressed as a matrix equation given by $$\vec{N}_{Det} = \underline{R} \vec{N}_{In},$$

where $$\underline{R} = \begin{bmatrix} R_{1,1}^{(0)} & R_{1,2}^{(0)} & R_{1,3}^{(0)} & R_{1,4}^{(0)} & R_{1,5}^{(0)} \\ R_{2,1}^{(0)} & R_{2,2}^{(0)} & R_{2,3}^{(0)} & R_{2,4}^{(0)} & R_{2,5}^{(0)} \\ R_{3,1}^{(0)} & R_{3,2}^{(0)} & R_{3,3}^{(0)} & R_{3,4}^{(0)} & R_{3,5}^{(0)} \\ R_{4,1}^{(0)} & R_{4,2}^{(0)} & R_{4,3}^{(0)} & R_{4,4}^{(0)} & R_{4,5}^{(0)} \\ R_{5,1}^{(0)} & R_{5,2}^{(0)} & R_{5,3}^{(0)} & R_{5,4}^{(0)} & R_{5,5}^{(0)} \end{bmatrix}, \vec{N}_{Det} = \begin{bmatrix} N_1^{(Det)} \\ N_2^{(Det)} \\ N_3^{(Det)} \\ N_4^{(Det)} \\ N_5^{(Det)} \end{bmatrix}, \text{ and }$$

$$\vec{N}_{In} = \begin{bmatrix} N_1^{(In)} \\ N_2^{(In)} \\ N_3^{(In)} \\ N_4^{(In)} \\ N_5^{(In)} \end{bmatrix}.$$

The linear response corrected counts $\vec{N}_{In}$ can be obtained by inverting the matrix $\underline{R}$ to solve the matrix equation, as given by $$\vec{N}_{In} = \underline{R}^{-1} \vec{N}_{Det}.$$

In one implementation, the first correction step is correcting for the nonlinear detector response to obtain the nonlinear corrected counts, $$\vec{N}_{Det} = \vec{N}_{Corr} = [N_1^{Corr.} N_2^{Corr.} N_3^{Corr.} N_4^{Corr.} N_5^{Corr.}]^T,$$

where T denotes the transpose. The second correction step is correcting for the linear detector response to obtain $$\vec{N}_{In} = \underline{R}^{-1} \vec{N}_{Det}.$$

Figure 6:
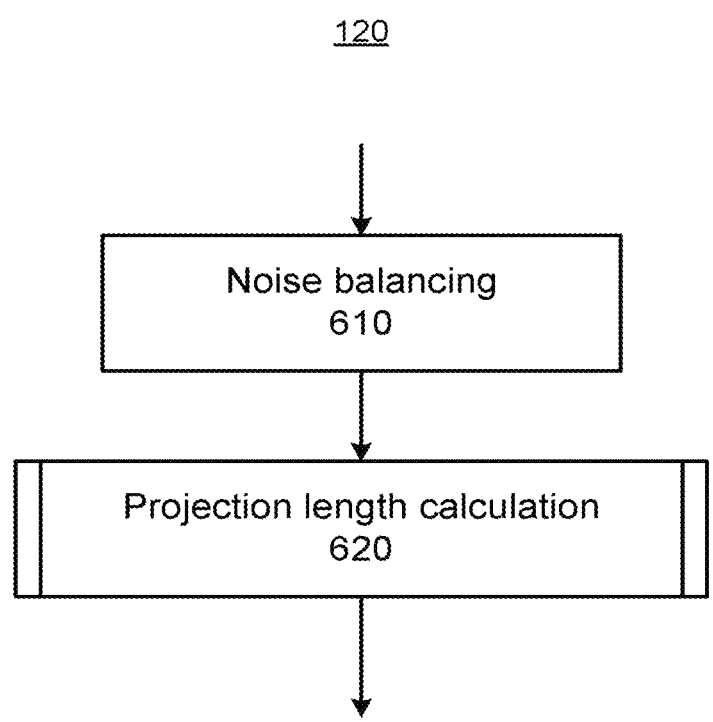
FIG. 6 shows a flow diagram of an implementation of a basis material decomposition method.

After correcting for the detector response, the next step is the basis material decomposition 120. As shown in FIG. 6, the material decomposition process 120 begins with the step of apportioning the counts from the multiple energy bins into two energy components corresponding to a high spectrum $S_H(E)$ and a low spectrum $S_L(E)$. The noise balancing process of apportioning the counts into high- and low-energy components is described in U.S. patent application Ser. No. 13/906,110, incorporated herein by reference in its entirety. Noise balancing enables the delineation between the high spectrum and the low spectrum to be different for different detectors in order to prevent the case where the signal to noise ratio for either the high- or low-energy components counts became significantly lower than the other energy component (i.e., the signal-to-noise ratio of the high- and low-energy components become unbalanced) and degrades the image quality of the reconstructed image.

In FIG. 6, the noise balancing in step 610 results in partitioning the counts from the energy bins into high- and low-energy components according to $$N_H = \sum_m a_m^{(H)} N_m^{Corr.}, \text{ and}$$

$$N_L = \sum_m a_m^{(L)} N_m^{Corr.},$$

where $a_m^{(H)} + a_m^{(L)} = 1$ and the values $a_m^{(H)}$ and $a_m^{(L)}$ are determined by noise balancing.

In an alternative implementation, the values $a_m^{(H)}$ and $a_m^{(L)}$ are predetermined values that are not determined by a noise-balancing process.

The next step 620 is the projection length calculation, and includes the process of decomposing the high- and low-energy components projection data into projection lengths of high- and low-Z materials, as described in Yu Zou and Michael Silver, "Analysis of fast kV-switching in dual energy CT using a pre-reconstruction decomposition technique," Proc. SPIE Vol. 6913, 691313-1 (2008), incorporated herein by reference in its entirety. One implementation of the material decomposition method of process 620 is also discussed in U.S. patent application Ser. No. 10/0,189,212, incorporated herein by reference in its entirety.

Figure 7:
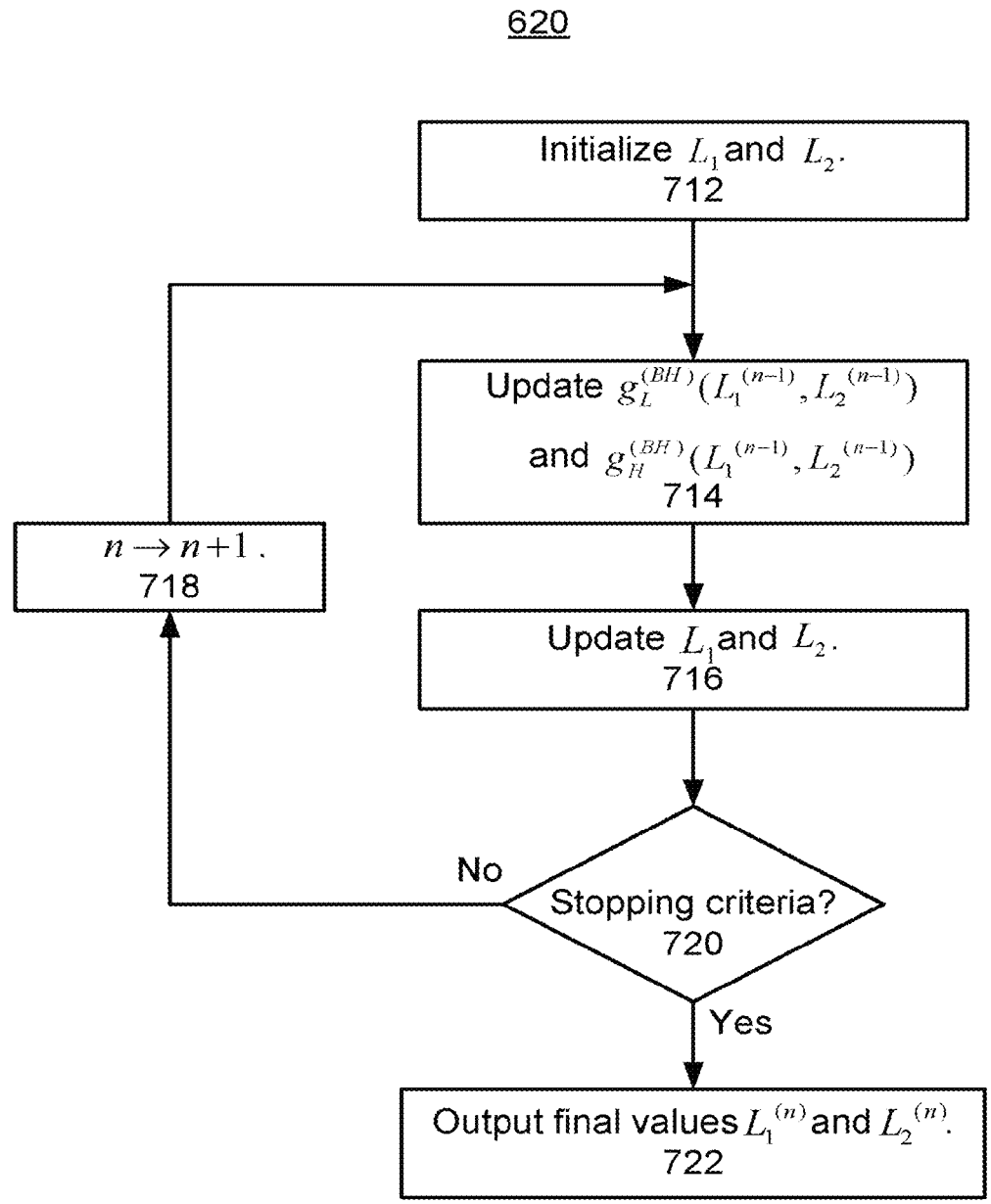
FIG. 7 shows a flow diagram of an implementation of a projection length calculation method.

One implementation of the process 620 for material decomposition is shown in FIG. 7. Similar to the detector counts for the high- and low-energy components, the high and low spectra can be given by $$S_H(E) = \sum_m a_m^{(H)} S_{air}(E), \text{ and}$$

$$S_L(E) = \sum_m a_m^{(L)} S_{air}(E),$$

where $S_H(E)$ and $S_L(E)$ are respectively the detected high- and low-energy spectra in the absence of the object OBJ (i.e., the object OBJ is air), and where $S_H(E)$ and $S_L(E)$ have been normalized such that $$\int dE S_H(E) = \int dE S_L(E) = 1.$$

By taking the natural logarithm of the detector counts, the log-projection data are obtained as $$g_H(l) = -\ln(N_H/N_H^{air}) \text{ and}$$

$$g_L(l) = -\ln(N_L/N_L^{air}),$$

where the path length l signifies the trajectory corresponding to the path integral/Radon transform of the X-rays incident on a given detector element.

In one implementation, as shown in FIG. 7, $L_1$ and $L_2$ are found using perturbation theory by treating the variations around the mean of the attenuation coefficients $\mu_1(E)$ and $\mu_2(E)$ as perturbations. First, the mean attenuation for the high- and low-energy spectra are given by $$\bar{\mu}_{1,2}^{H,L} = \int S_{H,L}(E)\mu_{1,2}(E)dE,$$

and the variations around the mean are given by $$\Delta\mu_{1,2}^{H,L}(E) = \mu_{1,2}(E) - \bar{\mu}_{1,2}^{H,L}.$$

Thus, the log-projection data can be expressed as $$g_H(l) = -\ln\int S_H(E)\exp[-\bar{\mu}_1^H L_1(l) - \Delta\mu_1^H(E)L_1(l) - \bar{\mu}_2^H L_2(l) - \Delta\mu_2^H(E)L_2(l)]dE$$

$$g_L(l) = -\ln\int S_L(E)\exp[-\bar{\mu}_1^L L_1(l) - \Delta\mu_1^L(E)L_1(l) - \bar{\mu}_2^L L_2(l) - \Delta\mu_2^L(E)L_2(l)]dE.$$

Simplifying these expressions, the log-projection data can be written as $$g_H(l) = \bar{\mu}_1^H L_1(l) + \bar{\mu}_2^H L_2(l) - g_H^{(BH)}(L_1(l), L_2(l))$$

$$g_L(l) = \bar{\mu}_1^L L_1(l) + \bar{\mu}_2^L L_2(l) - g_L^{(BH)}(L_1(l), L_2(l))$$

where $$g_{H,L}^{(BH)}(L_1(l),L_2(l)) \equiv \ln\int S_{H,L}(E)\exp[-L_1(l)\Delta\mu_1^{H,L}(E) - L_2(l)\Delta\mu_2^{H,L}(E)]dE$$

is the beam-hardening perturbation.

The first step 712 of process 620 is initializing n=0 and also initializing the values $L_1$ and $L_2$ to their respective zeroth order perturbation values by solving the matrix equation $$\begin{pmatrix} g_H \\ g_L \end{pmatrix} = \begin{pmatrix} \bar{\mu}_1^H & \bar{\mu}_2^H \\ \bar{\mu}_1^L & \bar{\mu}_2^L \end{pmatrix}\begin{pmatrix} L_1 \\ L_2 \end{pmatrix}$$

to obtain $$\begin{pmatrix} L_1 \\ L_2 \end{pmatrix} = D^{-1}\begin{pmatrix} \bar{\mu}_2^L & -\bar{\mu}_2^H \\ -\bar{\mu}_1^L & \bar{\mu}_1^H \end{pmatrix}\begin{pmatrix} g_H \\ g_L \end{pmatrix}$$

where D is the determinant $D = \bar{\mu}_1^H \bar{\mu}_2^L - \bar{\mu}_1^L \bar{\mu}_2^H$.

The second step 714 of process 620 and the first step in the iterative loop is updating the beam-hardening perturbation values using the $n^{th}$ order perturbation in the equation $$g_{H,L}^{(BH)}(L_1(l),L_2(l)) \equiv \ln\int S_{H,L}(E)\exp[-L_1(l)\Delta\mu_1^{H,L}(E) - L_2(l)\Delta\mu_2^{H,L}(E)]dE.$$

The third step 716 of process 620 is to update the values of $L_1$ and $L_2$ by solving for the n+1$^{th}$ perturbation by solving the matrix equation $$\begin{pmatrix} g_H + g_H^{(BH)}(L_1, L_2) \\ g_L + g_L^{(BH)}(L_1, L_2) \end{pmatrix} = \begin{pmatrix} \bar{\mu}_1^H & \bar{\mu}_2^H \\ \bar{\mu}_1^L & \bar{\mu}_2^L \end{pmatrix}\begin{pmatrix} L_1 \\ L_2 \end{pmatrix}$$

to obtain $$\begin{pmatrix} L_1^n \\ L_2^n \end{pmatrix} = D^{-1}\begin{pmatrix} \bar{\mu}_2^L & -\bar{\mu}_2^H \\ -\bar{\mu}_1^L & \bar{\mu}_1^H \end{pmatrix}\begin{pmatrix} g_H + g_H^{(BH)}(L_1^{n-1}, L_2^{n-1}) \\ g_L + g_L^{(BH)}(L_1^{n-1}, L_2^{n-1}) \end{pmatrix}.$$

After step 718, step 720 of process 620 inquiries whether stopping criteria have been satisfied. In one implementation, the stopping criteria are satisfied when the values $L_1$ and $L_2$ have adequately converged according to some predetermined criteria, such as whether the difference between each current and previous values of $L_1$ and $L_2$ are less than a predefined threshold, or whether a maximum number of iterations has been reached. If stopping criteria have not been satisfied, then the loop variable n is incremented at step 718 and the loop begins again starting from step 714.

The process 620 of process 120 provides new values of the projection lengths $L_1$ and $L_2$ different from the original projection length values used to calculate the nonlinear correction in process 110 shown in FIG. 1. An iterative process of feeding back the projection lengths calculated in the material decomposition process 120 back to the beginning of process 110 and repeating processes 110 and 120 multiple times will result in convergence to an optimal value for the projection lengths.

Figure 8:
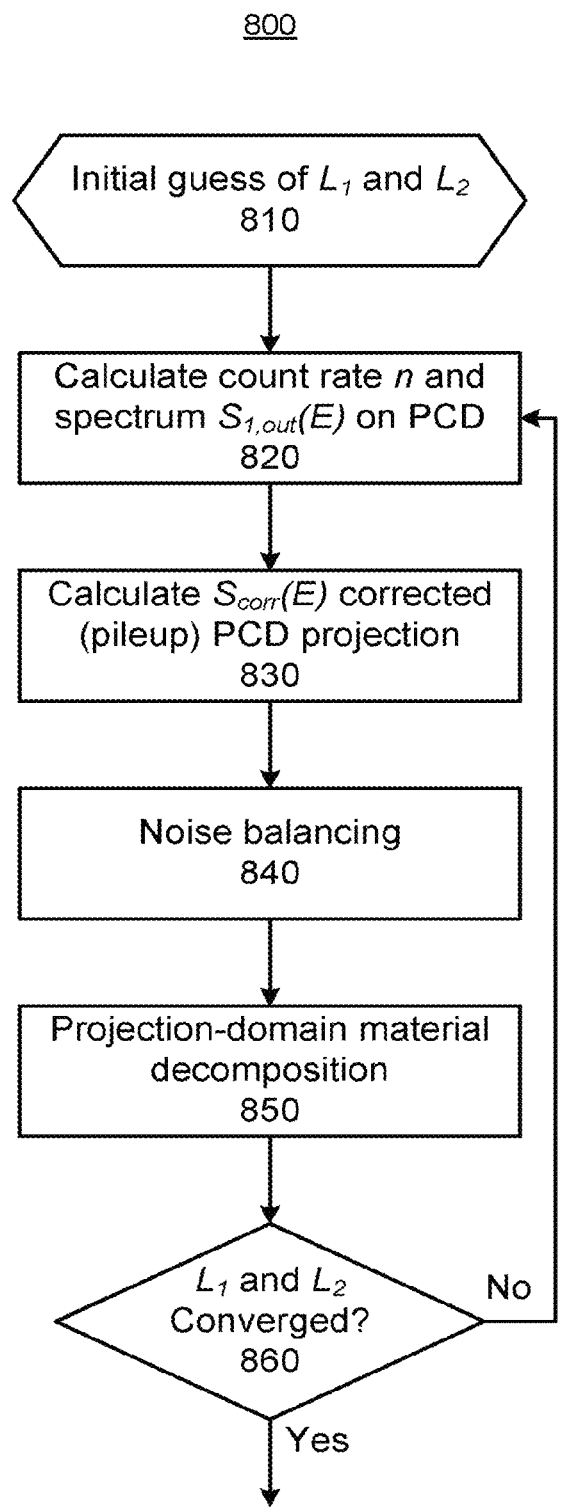
FIG. 8 shows a flow diagram of an implementation of an iterative detector response correction and material decomposition method.

Therefore, in one implementation, as shown in FIG. 8, the projection lengths $L_1$ and $L_2$ from the material decomposition step 850 will be fed back to the projection data correction step 820 and steps 820 through 850 are repeated again and again until the projection lengths converge such that the projection lengths remain essentially unchanged from the beginning of step 820 through the end of step 850.

FIG. 8 shows a single iterative method 800 replacing both the projection data correction process 110 and the basis material decomposition process 120. The method 800 begins at step 810 with an initial guess of the projection lengths $L_1$ and $L_2$ for a given PCD and a given projection measurement angle. The loop begins at step 820 by calculating the count rate $$n = n_{air}\int dE_0 S_{air}(E_0)\exp[-\mu_1(E_0)L_1 - \mu_2(E_0)L_2],$$

and the nonlinear correction term (e.g., $S_{Nonlin.}(E)$), which in the implementation shown in FIG. 8 includes only the first order pileup (i.e., two detection events within the detection window) given by $$S_{1,out}(E) = \iint dE_0 dE_1 R_1(E, E_0, E_1) S_{in}(E_0) S_{in}(E_1),$$

wherein $$S_{in}(E) = S_{air}(E)\exp[-\mu_1(E)L_1 - \mu_2(E)L_2].$$

Next at step 830 of method 800, the corrected detector spectrum is calculated correcting for pileup according to $$S_{Corr.}(E) = S_{Raw}(E) - S_{Nonlin.}(E).$$

The method 800 then proceeds to step 840, wherein noise balancing is performed by mapping the detector counts into high- and low-energy components in preparation for material decomposition. Material decomposition is then performed in step 850, wherein new values for the projection lengths $L_1$ and $L_2$ are calculated.

Finally, at step 860, an inquiry is made into whether the stopping criteria have been satisfied. The stopping criteria can include, e.g., conditions regarding whether the projection lengths $L_1$ and $L_2$ have converged, and whether the maximum number of loop iterations have been reached.

The material decomposition step 850 has a loop (referred to herein as the small loop)—given by process 620 as shown in FIG. 6—with its own stopping criteria. The small-loop stopping criteria of the step 850 may depend on the current iteration number of the large loop (i.e., the large being the loop that includes steps 820 through 860). For example, in one implementation, the step 850 loop can have a lower number of maximum iterations and more relaxed convergence threshold when the large-loop iteration variable is small, preventing the small loop in step 850 from spending an excessive time optimizing the projection lengths when the value of the projection lengths are at best rough approximations based on the bigger picture of the status of the large loop.

After obtaining the projections lengths by either exiting step 860 of method 800 or by completing process 120 in method 100, the projection lengths are prepared for further processing.

In a CT process, the projection lengths are processed by reconstructing an image from the projection lengths, as illustrated in process 130 of method 100 shown in FIG. 1. The image reconstruction process can be performed using filtered back-projection, iterative image reconstruction methods, or stochastic image reconstruction methods. After reconstructing an image of the object OBJ, the CT process then proceeds to the post-processing and image presentation steps as discussed in relation to FIG. 1.

In a non-CT application, such as radiography where the projection image is the final result, the data processing method proceeds directly from the material decomposition process 120 (or alternatively step 860 of method 800) to the post-processing 140 and image presentation 150 steps illustrated in FIG. 1.

Figure 9:
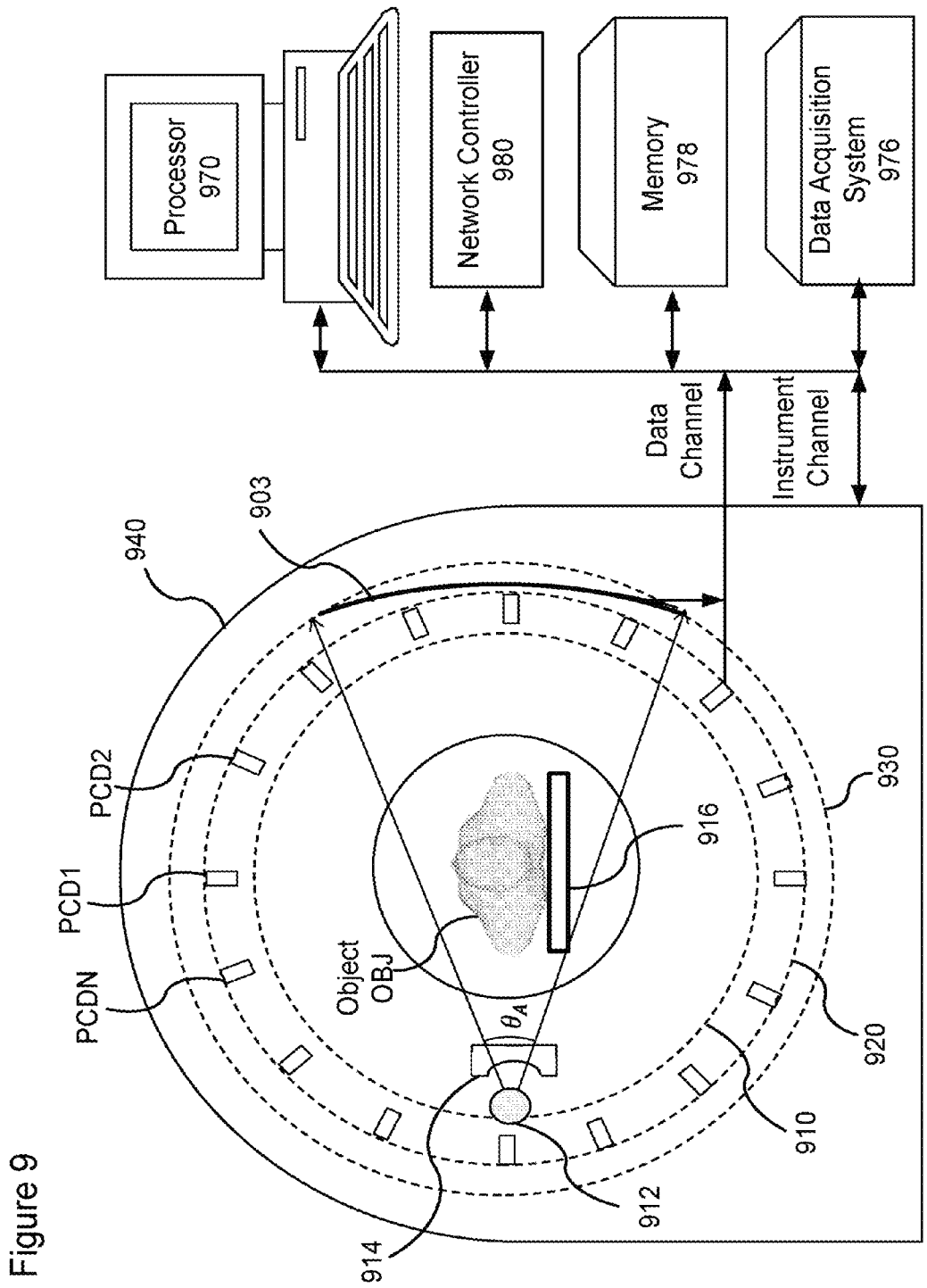
FIG. 9 shows a schematic of an implementation of a computed tomography scanner.

FIG. 9 shows a computed tomography (CT) scanner having both energy-integrating detectors arranged in a third-generation geometry and photon-counting detectors arranged in a fourth-generation geometry. Illustrated in FIG. 9 is an implementation for placing the photon-counting detectors (PCDs) in a predetermined fourth-generation geometry in combination with a detector unit 903 in a predetermined third-generation geometry in a CT scanner system. The diagram illustrates relative positions among an object OBJ to be scanned resting on a table 916, an X-ray source 912, a collimator/filter 914, an X-ray detector 903, and the photon-counting detectors PCD1 through PCDN in a gantry 940. Also shown in FIG. 9 is circuitry and hardware for acquiring, storing, processing, and distributing X-ray projection data. The circuitry and hardware include: a processor 970, a network controller 980, a memory 978, and a data acquisition system 976.

In one implementation, the CT scanner includes PCDs but does not include an energy-integrating detector unit 903

In general, the photon-counting detectors PCD1 through PCDN each output a photon count for each of a predetermined number of energy bins. In addition to the photon-counting detectors PCD1 through PCDN arranged in the fourth-generation geometry, the implementation shown in FIG. 9 includes a detector unit 903 having energy-integrating detectors arranged in a conventional third-generation geometry. The detector elements in the detector unit 903 can be more densely placed along the detector unit surface than the photon-counting detectors.

In one implementation, the photon-counting detectors are sparsely placed around the object OBJ in a predetermined geometry such as a circle. For example, the photon-counting detectors PCD1 through PCDN are fixedly placed on a predetermined circular component 920 in the gantry 940. In one implementation, the photon-counting detectors PCD1 through PCDN are fixedly placed on the circular component 920 at predetermined equidistant positions. In an alternative implementation, the photon-counting detectors PCD1 through PCDN are fixedly placed on the circular component 910 at predetermined non-equidistant positions. The circular component 920 remains stationary with respect to the object OBJ and does not rotate during the data acquisition.

Both the X-ray source 912, collimator 914 (e.g., a bow tie filter), and the detector unit 903 rotate around the object OBJ while the photon-counting detectors PCD1 through PCDN are stationary with respect to the object OBJ. In one implementation, the X-ray source 912 and collimator 914 are mounted on a first rotating portion 910 such as the annular frame in the gantry 940 so that the X-ray source 912 projects X-ray radiation with a predetermined source fan beam angle $\theta_A$ towards the object OBJ while the X-ray source 912 rotates around the object OBJ inside the sparsely placed photon-counting detectors PCD1 through PCDN. Furthermore, an additional detector unit 903 is mounted on a second rotating portion 930 in the third-generation geometry. The rotating portion 930 mounts the detector unit 903 at a diametrically opposed position from the X-ray source 912 across the object OBJ and rotates outside the stationary circular component 920, on which the photon-counting detectors PCD1 through PCDN are fixedly placed in a predetermined sparse manner.

In one implementation, the X-ray source 912 optionally travels a helical path relative to the object OBJ, which is moved in a predetermined direction that is perpendicular to the rotational plane of the rotating portion 910.

As the X-ray source 912 and the detector unit 903 rotate around the object OBJ, the photon-counting detectors PCDs and the detector unit 903 respectively detect the transmitted X-ray radiation during data acquisition. The photon-counting detectors PCD1 through PCDN intermittently detect the X-ray radiation that has been transmitted through the object OBJ and individually output a count value representing a number of photons, for each of the predetermined energy bins. On the other hand, the detector elements in the detector unit 903 continuously detect the X-ray radiation that has been transmitted through the object OBJ and output the detected signals as the detector unit 903 rotates. In one implementation, the detector unit 903 has densely placed energy-integrating detectors in predetermined channel and segment directions on the detector unit surface.

In one implementation, the X-ray source 912, the photon-counting detectors and the detector unit 903 collectively form three predetermined circular paths that differ in radius. The photon-counting detectors are sparsely placed along a first circular path around the object OBJ while at least one X-ray source 912 rotates along a second circular path around the object OBJ. Further, the detector unit 903 travels along a third circular path. The above exemplary embodiment illustrates that the third circular path is the largest and outside the first and second circular paths around the object OBJ. Although not illustrated, an alternative embodiment optionally changes the relative relation of the first and second circular paths so that the second circular path for the X-ray source 912 is larger and outside the first circular path of the sparsely placed photon-counting detectors PCD1 through PCDN around the object OBJ. Furthermore, in another alternative embodiment, the X-ray source 912 also optionally travels on the same third circular path as the detector unit 903.

There are other alternative embodiments for placing the photon-counting detectors in a predetermined fourth-generation geometry in combination with the detector unit in a predetermined third-generation geometry in the CT scanner. Several alternative embodiments of the X-ray CT Scanner as described in U.S. patent application Ser. No. 13/0,291,097, herein incorporated by reference in its entirety.

In one implementation, the X-ray source 912 is optionally a single energy source in certain embodiments. In another implementation, the X-ray source 912, which is configured to perform a kV-switching function for emitting X-ray radiation at a predetermined high-level energy and at a predetermined low-level energy. In still another alternative embodiment, the X-ray source 912 is a single source emitting a broad spectrum of X-ray energies. In still another embodiment, the X-ray source 912 is more than a single X-ray emitter and each emitter can emit X-rays separately and emits a different spectrum of X-ray energies.

The detector unit 903 can use energy integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline (e.g., NaI(Tl), CsI (Tl), CsI(Na), CsI(pure), CsF, KI(Tl), LiI(Eu), $BaF_2$, $CaF_2$ (Eu), ZnS(Ag), $CaWO_4$, $CdWO_4$, YAG(Ce), $Y_3Al_5O_{12}$(Ce), GSO, LSO, $LaCl_3$(Ce), $LaBr_3$(Ce), LYSO, BGO, $LaCl_3$ (Ce), $LaBr_3$(Ce), $C_{14}H_{10}$, $C_{14}H_{12}$, and $C_{10}H_8$), an organic liquid (e.g., an organic solvent with a fluor such as p-terphenyl ($C_{18}H_{14}$), PBD ($C_{20}H_{14}N_2O$), butyl PBD ($C_{24}H_{22}N_2O$), or PPO ($C_{15}H_{11}NO$)), a plastic (e.g., a flour suspended in a solid polymer matrix), or other know scintillator.

The photon-counting detectors can use a direct X-ray radiation detectors based on semiconductors, such as cadmium telluride (CdTe), cadmium zinc telluride (CZT), silicon (Si), mercuric iodide ($HgI_2$), and gallium arsenide (GaAs), which have much faster time response than indirect detectors. The fast time response of direct detectors enables them to resolve individual X-ray detection events with only limited pile-up even at the high X-ray fluxes typical of clinical X-ray imaging applications. The amount of energy of the X-ray detected is proportional to the signal generated at the direct detector, and the energies of detection events can be binned into a discrete number of corresponding energy bins yielding spectrally resolved X-ray projection measurements.

The CT scanner also includes a data channel that routes projection measurement results from the photon counting detectors and the detector unit 903 to a data acquisition system 976, a processor 970, memory 978, network controller 980. The data acquisition system 976 controls the acquisition, digitization, and routing of projection data from the detectors. The data acquisition system 976 also includes radiography control circuitry to control the rotation of the annular rotating frames 910 and 930. In one implementation data acquisition system 976 will also control the movement of the bed 916, the operation of the X-ray source 912, and the operation of the X-ray detectors 903. The data acquisition system 976 can be a centralized system or alternatively it can be a distributed system. In an implementation, the data acquisition system 976 is integrated with the processor 970.

The processor 970 performs functions including reconstructing images from the projection data, pre-reconstruction processing of the projection data, and post-reconstruction processing of the image data. The pre-reconstruction processing of the projection data can include correcting for detector calibrations, detector nonlinearities, polar effects, noise balancing, and material decomposition. Post-reconstruction processing can include filtering and smoothing the image, volume rendering processing, and image difference processing as needed. The image reconstruction process can be performed using filtered back projection, iterative image reconstruction methods, or stochastic image reconstruction methods. Both the processor 970 and the data acquisition system 976 can make use of the memory 976 to store, e.g., projection data, reconstructed images, calibration data and parameters, and computer programs.

The processor 970 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 978 can be a hard disk drive, CD-ROM drive, DVD drive, FLASH drive, RAM, ROM or any other electronic storage known in the art.

The network controller 980, such as an Intel Ethernet PRO network interface card from Intel Corporation of America, can interface between the various parts of the CT scanner. Additionally, the network controller 980 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus to process projection measurements, the apparatus comprising:
processing circuitry configured to
obtain a plurality of datasets, wherein each dataset represents radiation detected by a detector having a plurality of detector elements, the radiation having been transmitted through an object, wherein each dataset corresponds to a respective energy bin having an energy-detection spectrum that is narrower than a bandwidth of an energy spectrum of the transmitted radiation;
calculate a nonlinear detector response of each dataset and subtract the nonlinear detector response from the dataset to obtain a corresponding linear-response dataset, wherein the nonlinear detector response being a response of the detector in which an output of the detector varies nonlinearly with respect to an input of the detector; and
perform a material decomposition of the plurality of linear-response datasets into a plurality of projection lengths of a first material and a second material.

2. The apparatus according claim 1, wherein the processing circuitry is further configured to obtain the plurality of datasets, which represent the detection of X-ray radiation.

3. The apparatus according claim 2, wherein the processing circuitry is further configured to:
calculate the nonlinear detector response using a detector response model, which includes at least one of pileup effects and ballistic deficit effects, polar effects, and characteristics X-ray escape effects.

4. The apparatus according claim 3, wherein the processing circuitry is further configured to:
calculate the nonlinear detector response of each respective detector element of the detector using a corresponding nonlinear response function including a dead time of the corresponding detector element $\tau$, a quadratic response function of the corresponding detector element $R_1$, an X-ray flux at the corresponding detector element, and an incident spectrum that is a spectrum of the energies of the X-rays incident on the corresponding detector element.

5. The apparatus according claim 4, wherein the processing circuitry is further configured to calculate the nonlinear detector response using the X-ray flux at a detector element of the detector that is determined using a reference intensity representing an X-ray intensity at an X-ray source that is related to the X-ray flux at the detector element using a corresponding intensity calibration value A, and the X-ray flux at the detector element and the incident spectrum are each calculated using the plurality of projection lengths, which includes a projection length of the first material and a projection length of the second material.

6. The apparatus according claim 5, wherein the processing circuitry is further configured to:
calibrate the plurality of detector elements by determining calibration values, including the detector response model, using calibration data that includes the dead time $\tau$ of each respective detector element of the detector, the quadratic response function $R_1$ of each respective detector element, and the corresponding intensity calibration value A of each respective detector element;
wherein adjusting the calibration values changes a spectrum of the detector-response model, and
the calibration of the detector is performed in an iterative calibration loop by iteratively adjusting the calibration values until either a value returned by a cost function measuring the difference between a spectrum of the plurality of data sets and the spectrum of the detector-response model falls below a predefined threshold or a maximum number of calibration loop iterations is reached.

7. The apparatus according claim 2, wherein the processing circuitry is further configured to:
perform a material decomposition of the plurality of linear-response datasets using noise balancing to
combine the plurality of linear-response datasets into a low-energy projection-data component having a first X-ray energy spectrum, and
combine the plurality of linear-response datasets into a high-energy projection-data component having a second X-ray energy spectrum,
wherein an energy expectation value of the first X-ray energy spectrum is less than an energy expectation value of the second X-ray energy spectrum.

8. The apparatus according claim 7, wherein the processing circuitry is further configured to:
perform the material decomposition of the plurality of linear-response datasets into the plurality of projection lengths by calculating for each detector element of the plurality of detector elements a projection length of the first material and a projection length of the second material, wherein
the calculation of the plurality of projection lengths includes calculating perturbations of beam hardening corrections for variations of attenuation values of the first and second materials around mean attenuation values.

9. The apparatus according claim 2, further comprising:
a polychromatic X-ray source radiating X-rays;
a photon counting spectrally discriminating X-ray detector configured to detect the X-rays that are radiated from the X-ray source, where the X-ray detections are arranged into energy bins according to the detected energy of each X-ray detection, and each energy bin is assigned to a corresponding dataset of the plurality of datasets.

10. The apparatus according claim 2, wherein the processing circuitry is further configured to:
reconstruct a plurality of images using the plurality projection lengths of the first material and using the plurality projection lengths of the second material, where the reconstruction method is one of a filtered back-projection method, an iterative image-reconstruction method, and a statistical image-reconstruction method.

11. The apparatus according claim 2, wherein the processing circuitry is further configured to:
solve for the plurality of projection lengths of the first material and plurality of projection lengths of the first material by performing in an iterative loop the steps of calculating the nonlinear detector response and subtracting the nonlinear detector response from each respective dataset to obtain the corresponding linear-response dataset, and then performing the material decomposition on each linear-response dataset;

wherein the plurality of projection lengths of the first material and of the second material resulting from a previous iteration of material decomposition are used as the plurality of first and second material projection lengths for calculating the nonlinear detector response of a next iteration, and the iterative loop stops when a predefined stopping criteria is satisfied.

12. A computed tomography apparatus, comprising:

a radiation source configured to emit radiation toward an image object;

a detector having a plurality of detector elements configured to detect the radiation having been transmitted through the image object and to generate projection data representing an intensity of the radiation at the detector;

a rotation mount configured to rotate the radiation source around the image object, wherein the radiation source is fixedly connected to the rotation mount;

processing circuitry configured to obtain a plurality of datasets of the projection data, wherein each dataset represents radiation detected by the detector, the radiation having been transmitted through the image object, wherein each dataset corresponds to a respective energy bin having an energy detection spectrum that is narrower than a bandwidth of an energy spectrum of the transmitted radiation;

calculate a nonlinear detector response of each dataset and subtract the nonlinear detector response from the dataset to obtain a corresponding linear-response dataset, wherein the nonlinear detector response being a response of the detector in which an output of the detector varies nonlinearly with respect to an input of the detector; and perform a material decomposition of the plurality of linear-response datasets into a plurality of projection lengths of a first and a second material.

13. A method of processing X-ray projection data, comprising:

obtaining a plurality of datasets, wherein each dataset represents radiation detected by a detector having a plurality of detector elements, the radiation having been transmitted through an object, and each dataset corresponds to a respective energy bin having an energy detection spectrum that is narrower than a bandwidth of an energy spectrum of the transmitted radiation;

calculating a nonlinear detector response of each dataset and subtracting the nonlinear detector response from the dataset to obtain a corresponding linear-response dataset, wherein the nonlinear detector response being a response of the detector in which an output of the detector varies nonlinearly with respect to an input of the detector;

performing a material decomposition of the plurality of linear-response datasets into a plurality of projection lengths of a first and a second material.

14. The method according to claim 13, wherein the step of calculating a nonlinear detector response uses a detector response model for calculating at least one of the nonlinear detector response including pileup of detection events, ballistic deficit effects, polar effects, and characteristics X-ray escape effects.

15. The method according to claim 13, wherein the step of calculating a nonlinear detector response is calculated using a respective nonlinear response function of each corresponding detector element of the plurality of detector elements, the nonlinear response function including a dead time of the corresponding detector element $\tau$, a quadratic response function of the corresponding detector element $R_1$, an X-ray flux at the corresponding detector element, and an incident spectrum that is a spectrum of the energies of the X-rays incident on the corresponding detector element.

16. The method according to claim 15, further comprising:

calibrating the plurality of detector elements by determining calibration values, including the detector response model, using calibration data that includes the dead time $\tau$ of each respective detector element, the quadratic response function $R_1$ of each respective detector element, and the respective intensity calibration value A of each respective detector element;

wherein adjusting the calibration values changes a spectrum of the detector-response model, and the calibration of the plurality of detector elements is performed in an iterative calibration loop by iteratively adjusting the calibration values until either a value returned by a cost function measuring the difference between a spectrum of the plurality of data sets and the spectrum of the detector-response model falls below a predefined threshold or a maximum number of calibration loop iterations is reached.

17. A non-transitory computer-readable medium storing executable instructions, wherein the instructions, when executed by processing circuitry, cause the processing circuitry to perform the method according to claim 13.

* * * * *